United States Patent
Gergely et al.

(10) Patent No.: US 6,497,900 B2
(45) Date of Patent: *Dec. 24, 2002

(54) EFFERVESCENT BASE

(75) Inventors: Gerhard Gergely, Gartengasse 8, A-1053 Vienna (AT); Irmgard Gergely, Vienna (AT); Thomas Gergely, Vienna (AT); Stefan Gergely, Vienna (AT)

(73) Assignee: Gerhard Gergely, Vienna (AT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/529,343

(22) PCT Filed: Oct. 21, 1998

(86) PCT No.: PCT/EP98/06663
§ 371 (c)(1), (2), (4) Date: May 24, 2000

(87) PCT Pub. No.: WO99/20246
PCT Pub. Date: Apr. 29, 1999

(65) Prior Publication Data
US 2002/0150614 A1 Oct. 17, 2002

(30) Foreign Application Priority Data
Oct. 21, 1997 (CH) .............................. 2446/97
Oct. 28, 1997 (CH) .............................. 2488/97

(51) Int. Cl.$^7$ ................................ A61K 9/46
(52) U.S. Cl. ...................... 424/466; 424/489
(58) Field of Search .................... 424/466, 489, 424/439

(56) References Cited

U.S. PATENT DOCUMENTS

| | | | |
|---|---|---|---|
| 5,415,870 A | * | 5/1995 | Gergely et al. |
| 5,527,540 A | | 6/1996 | Gergely et al. |
| 5,603,920 A | | 2/1997 | Rice |
| 5,762,951 A | * | 6/1998 | Maasz et al. ............. 424/439 |

FOREIGN PATENT DOCUMENTS

| | | | |
|---|---|---|---|
| EP | 0 474 040 A1 | 3/1992 | |
| GB | 1 269 620 | 4/1972 | |
| JP | 4247025 | * 9/1992 | ............ A61K/9/14 |

* cited by examiner

Primary Examiner—Thurman K. Page
Assistant Examiner—Robert M. Joynes
(74) Attorney, Agent, or Firm—Oliff & Berridge, PLC

(57) ABSTRACT

The effervescent base for the preparation of effervescent tablets and effervescent granules consists of at least one acidic and one gas-evolving component, the former of which is formed by a mixture of (predominantly) monosodium tartrate and (possibly) disodium tartrate, and optionally tartaric acid. The effervescent base is prepared by mixing tartaric acid with sodium bicarbonate and sodium carbonate containing water of crystallization and slowly reacting the mixture at a temperature increasing to about 50° C., after which further sodium carbonate containing water of crystallization is admixed and is allowed to react up to a temperature of about 60° C., and drying is then carried out, preferably in vacuo, the mixture is mixed with further, now anhydrous sodium carbonate and the product is optionally pressed to give tablets. The base may additionally comprise an acid sensitive or an alkali-sensitive pharmaceutically active substance.

3 Claims, 6 Drawing Sheets

Change in dissolution time of tartaric acid effervescent system J15 according to the invention on storage in the humidity chamber (85% RH/22°C)

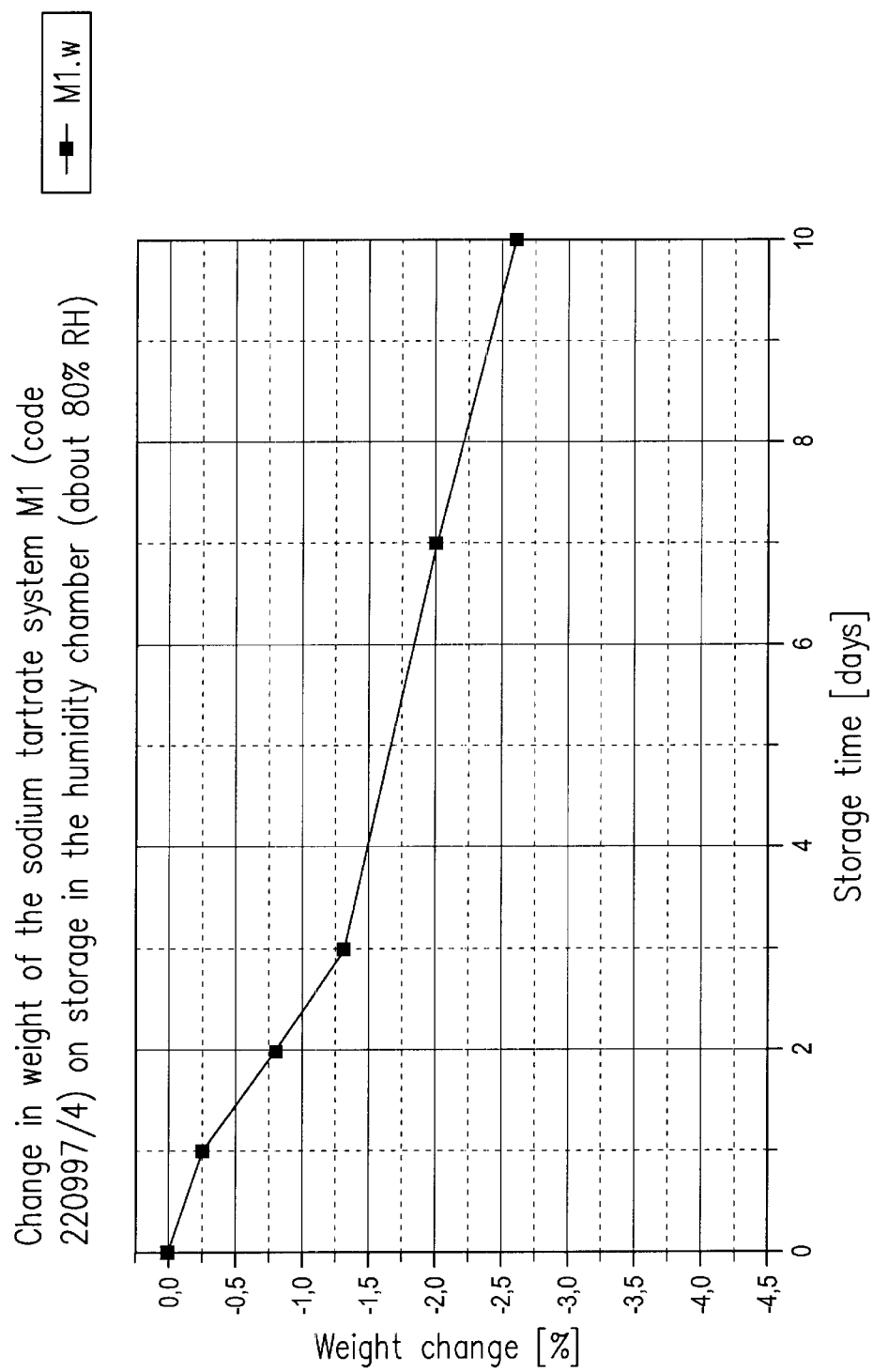

EFFERVESCENT BASE

It is known that particularly effervescent granules consisting of citric acid and sodium bicarbonate or sodium carbonate are relatively highly sensitive to atmospheric humidity, This is also true of systems in which sodium citrates are used with alkali metal bicarbonates and/or carbonates.

For instance, U.S. Pat. No. 5,415,870 teaches to simultaneously incorporate tartaric acid in the surface of citric acid carrier crystals. The crystal surface can be doped with tartaric acid and then be allowed to react with carbonates and/or bicarbonates.

Moreover, U.S. Pat. No. 5,527,540 suggests to use tartaric acid as carrier for effervescent system particles, Therefore sodium carbonate and sodium bicarbonate are embedded on crystalline tartaric acid and in powdered tartaric acid by granulation, whereupon the granules are covered with a solution of tartaric acid and EDTA.

Effervescent systems which are prepared using monosodium tartrate with alkali metal bicarbonates and/or carbonates are known to have improved properties, especially with respect to the sensitivity to atmospheric humidity. On the other hand, monosodium tartrate is very expensive.

Attempts have now been made to produce monosodium tartrate by reacting tartaric acid with sodium carbonate and bicarbonate by means of surface reactions.

Such surface reactions lead to mixed systems comprising monosodium tartrates and disodium tartrates. It has now surprisingly been found that relatively large amounts of monosodium tartrate are formed in surface reactions of this type, and it would have to be assumed that they give very slow effervescent systems.

On the other hand, it has been found that relatively substantial reaction of tartaric acid and resulting relatively large amounts of monosodium tartrate give very rapid effervescent systems which furthermore exhibit previously unknown stability to atmospheric humidity.

It was found, surprisingly, that the tartaric acid, which is converted to monosodium tartrate, with sodium bicarbonate gives surprisingly short dissolution times and in particular is stable to atmospheric humidity of 80% for 6 days or more.

The granules which are produced in the reaction of tartaric acid and sodium bicarbonate and sodium carbonate were scientifically investigated in order to clearly find out which salts predominantly occur and what is the reason for the insensitivity to moisture.

BRIEF DESCRIPTION OF THE DRAWINGS

FIG. 6 is a graph depicting the change in tablet weight of a sodium tartrate effervescent system versus the storage time in a humidity chamber.

The preparation principle is based on the fact that tartaric acid A's reacted with sodium carbonates having contents of water of crystallization and sodium bicarbonate at elevated temperatures, the tartaric acid being primarily converted into monosodium tartrate.

The reacted product is dried, preferably by means of vacuum, and although the system may contain a small amount of water of crystallization, it is extremely insensitive to atmospheric humidity with a dissolution time of 20–40 seconds. These effervescent granules which on the one hand are highly stable in relation to moisture while on the other hand have excellent dissolution properties were subjected to spectroscopic investigation and possible conclusions were drawn in regard to the reaction procedures.

First of all, IR-spectra of the individual components such as tartaric acid, sodium hydrogen tartrate, di-sodium tartrate and sodium hydrogen carbonate, were measured, which were used for comparisons for the granule material. It was possible to find that the effervescent formulation primarily comprises sodium hydrogen tartrate (monosodium tartrate) and carbonates, that is to say the tartaric acid is almost completely converted into monosodium tartrate and only small amounts are reacted to form di-sodium tartrate under given manufacturing conditions.

In order to substantiate this, the tartaric acid content in tablets and granules was determined gravimetrically after extraction of the tartaric acid with diethyl ether. In the experiments, practically no free tartaric acid or only quite small amounts of it could be isolated, and tartaric acid was also no longer to be found in the IR-spectra of the tablets and granules.

It is not only the conversion to monosodium tartrate but probably also crystal-chemical reasons that appear to be decisive aspects in terms of the stability of the system in effervescent tablets and the enhanced level of reactivity in regard to dissolution in water.

Preparation Process:

370 parts of tartaric acid, 240 parts of sodium bicarbonate and 20 parts of sodium carbonate with 10 molecules of water of crystallization are mixed and are slowly reacted at a temperature increasing from 30° C. to 54° C. On reaching about 54° C., a dried sample pressed to give tablets has a dissolution time of 300 seconds with a residual $CO_2$ content of 10% and a skeletal residue.

Another 25 parts of sodium carbonate with 10 molecules of water of crystallization are then introduced and reacted further up to a temperature of 55–60° C.

A dried sample, pressed to give tablets, has a dissolution time of 30 seconds with a residual $CO_2$ content of 5.50%. This low content of $CO_2$ furthermore indicates the very substantial conversion of tartaric acid into sodium tartrates.

After heating to 60° C., vacuum-drying is carried out. The dried mixture is furthermore mixed with anhydrous sodium carbonate in a ratio of 10:1 and has a pH of 4.5 in combination with dissolution times of 20–30 seconds.

Figure 1:
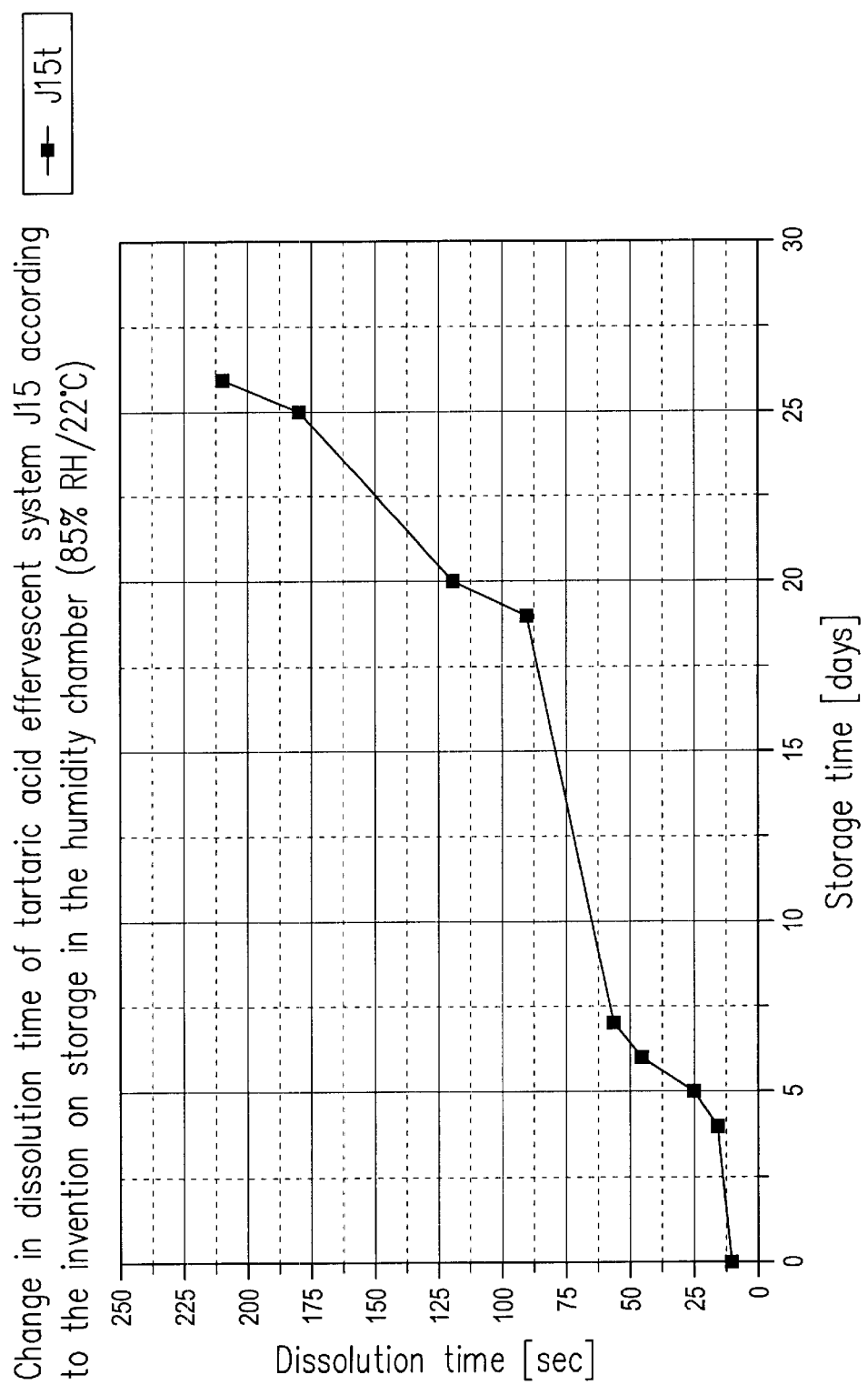
FIG. 1 is a graph depicting the change in dissolution time of a tartaric acid effervescent system versus the storage time in a humidity chamber.

The investigations of such tablets in a humidity chamber at 85% relative humidity and at a temperature of 22° C. are then extremely surprising. Table 1 shows the change in the dissolution time of tartaric acid effervescent system J15 according to the invention after storage in the humidity chamber. After 5 days, the dissolution time has scarcely changed and increases to about 100 seconds only after 20 days. It is only from 20 days onwards that the system dramatically slows down (FIG. 1).

Figure 2:
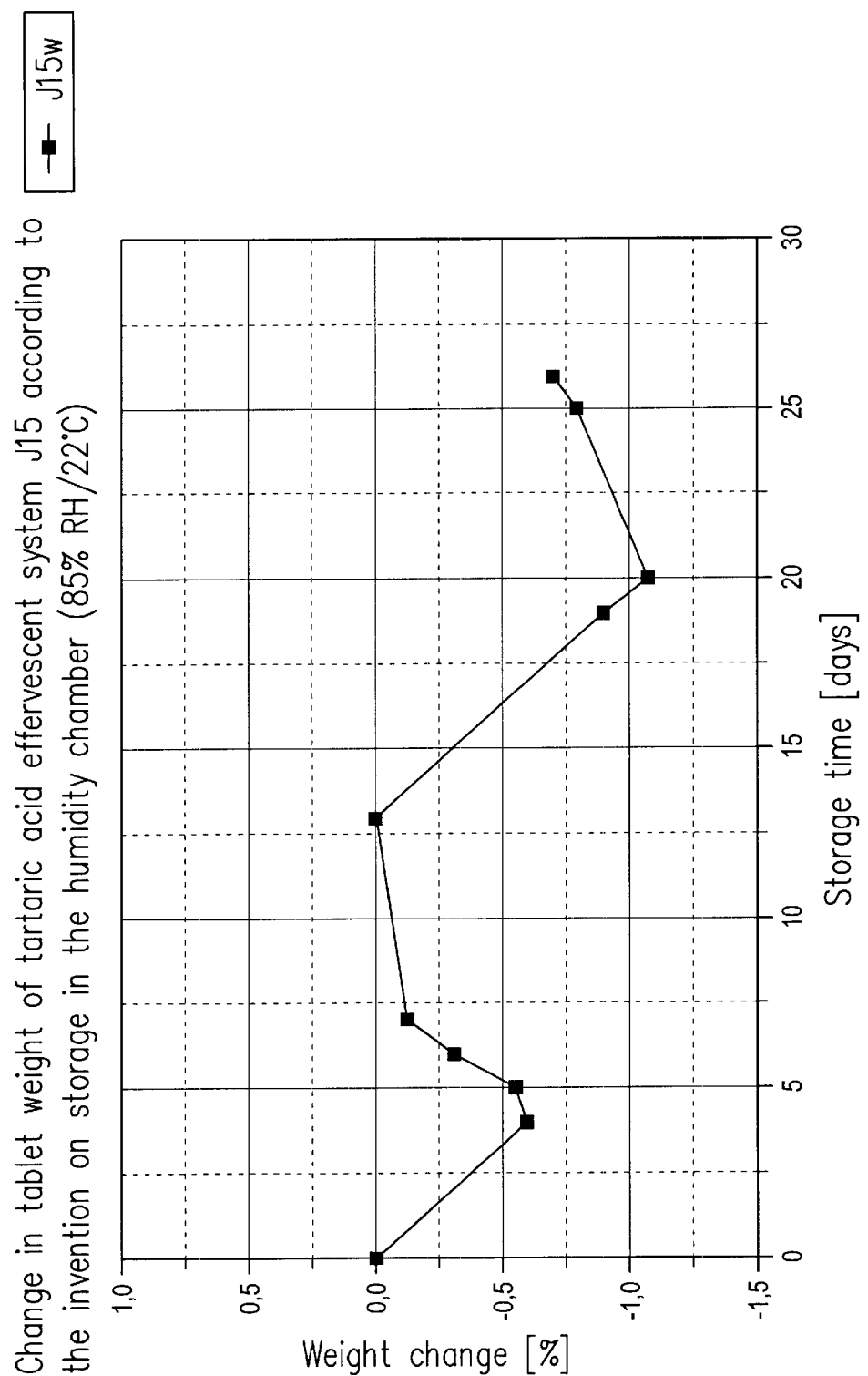
FIG. 2 is a graph depicting the change in tablet weight of a tartaric acid effervescent system versus the storage time in a humidity chamber.

Since the reactivity can also be determined by the change in tablet weight of tartaric acid effervescent system J15 according to the invention on storage in the humidity chamber, it is found that the tablet weight remains virtually unchanged for a storage time of 10 days or more and reaction occurs only after 15 days, the resulting $CO_2$ reducing the tablet weight (FIG. 2).

Figure 3:
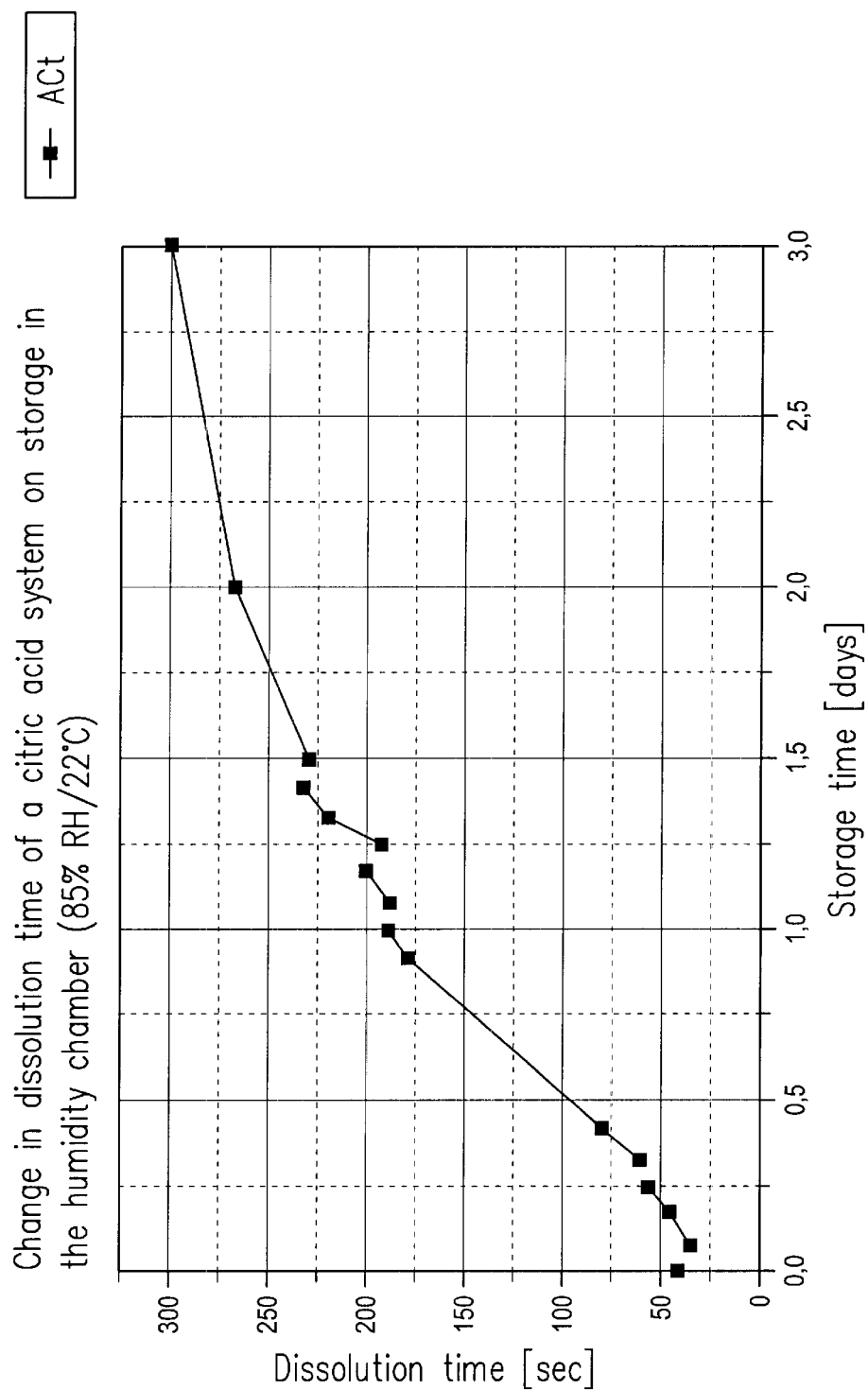
FIG. 3 is a graph depicting the change in dissolution time of a citric acid effervescent system versus the storage time in a humidity chamber.

If such a system is compared with passivated citric acid (after preliminary reaction with bicarbonate and superficial conversion into monosodium citrate) in the humidity chamber, an increase in the dissolution time by a factor of about 4 is found after only one day, and the system decomposes after a longer time (FIG. 3).

Figure 4:
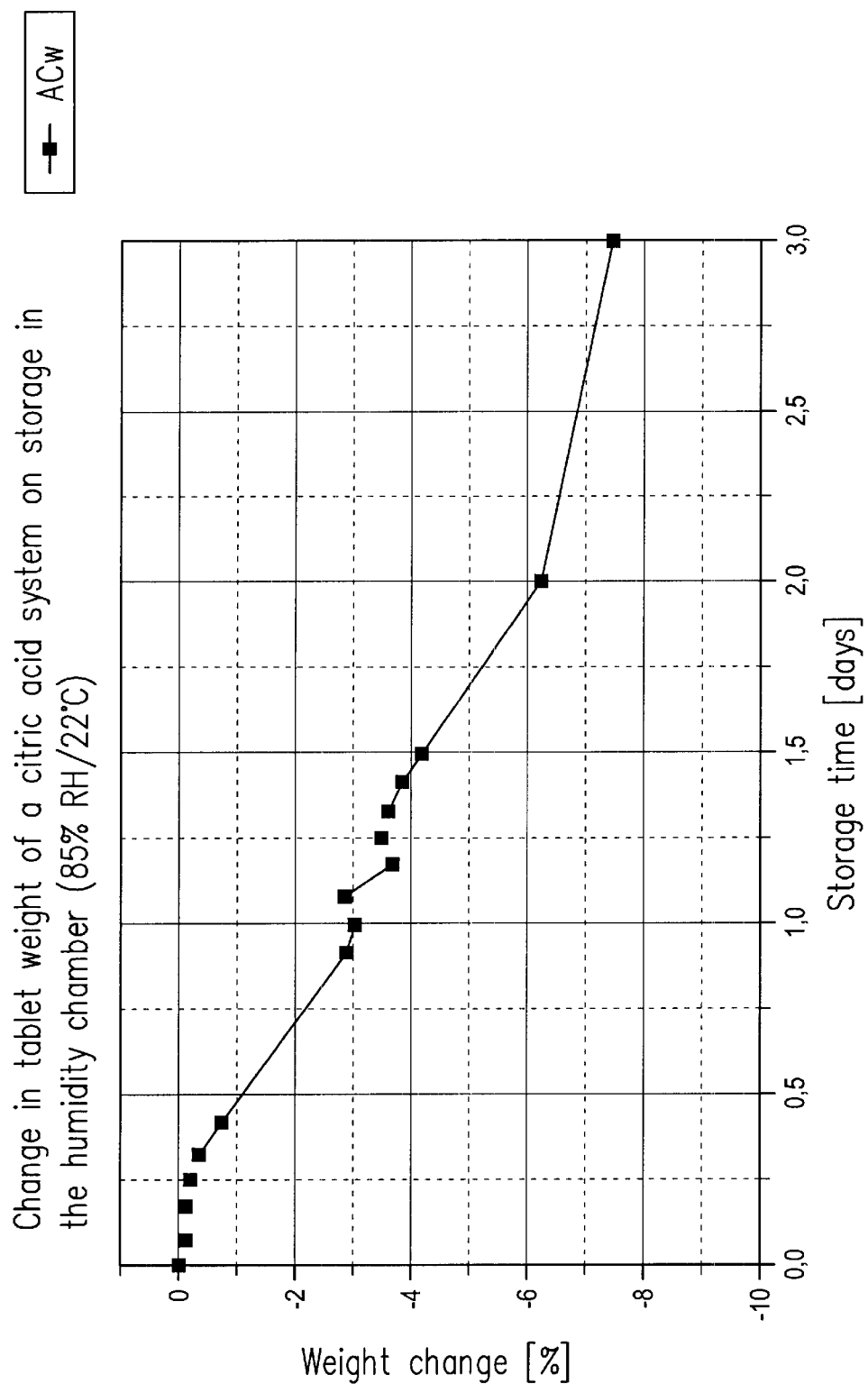
FIG. 4 is a graph depicting the change in tablet weight of a citric acid effervescent system versus the storage time in a humidity chamber.

The change in the tablet weight of a citric acid system on storage in the humidity chamber also shows the same trend, i.e. these systems are substantially more unstable than the tartaric acid/tartrate system (FIG. 4).

Figure 5:
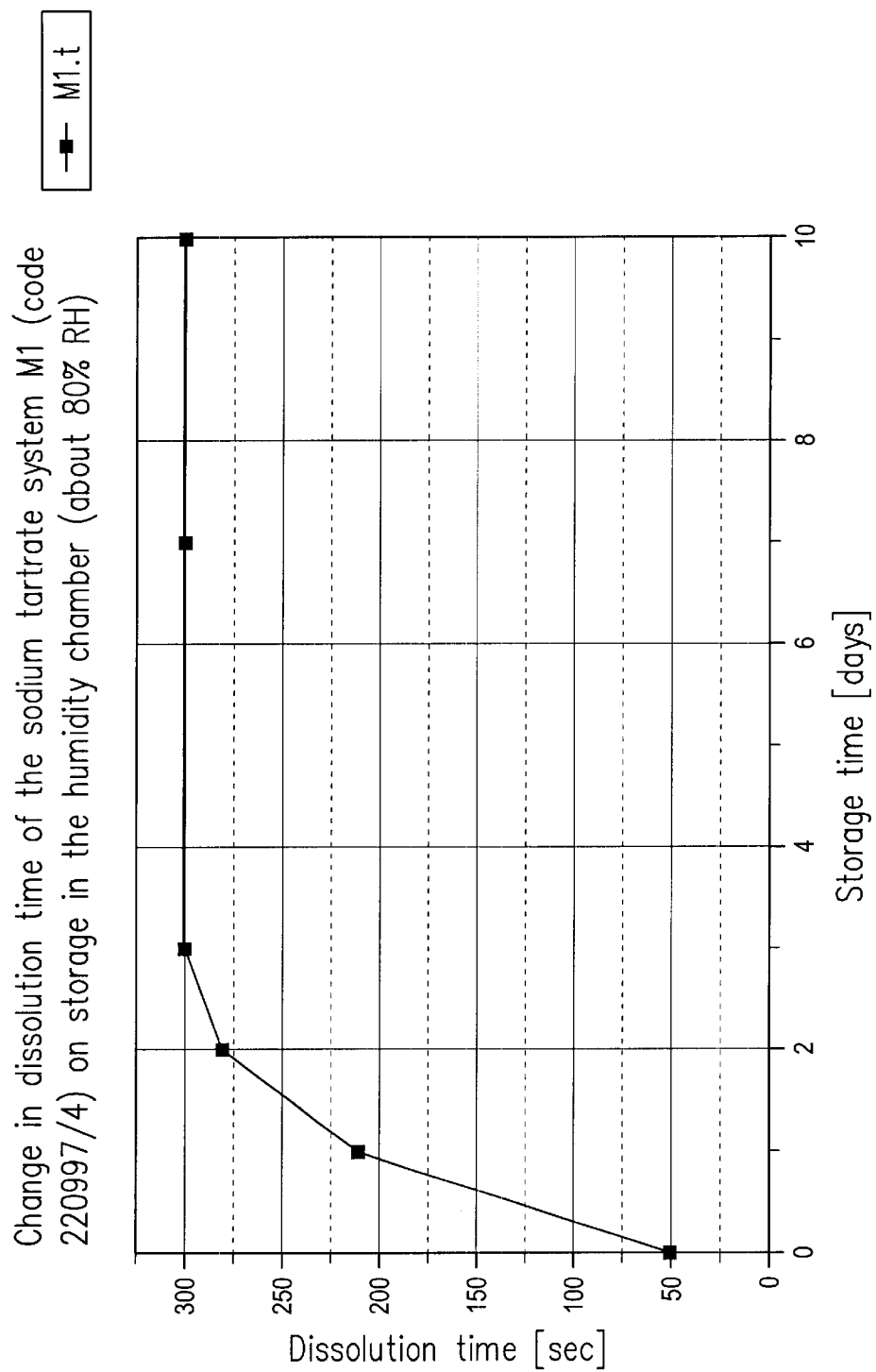
FIG. 5 is a graph depicting the change in dissolution time of a sodium tartrate effervescent system versus the storage time in a humidity chamber.

Furthermore, a comparison with a system consisting of monosodium tartrate and sodium bicarbonate has an initial dissolution time of about 50 seconds and relatively soon—after 2 days storage in the humidity chamber of about 80% relative humidity—of more than 250 seconds (FIG. 5).

In the humidity chamber at 80% relative humidity, too, the tablet of a sodium tartrate system M1 exhibits, as a result of a reaction and the $CO_2$ evolved thereby, weight loss and hence a relatively high sensitivity to atmospheric humidity (FIG. 6).

The use of the acid component according to the invention of an effervescent system mixed with alkali hydrogen carbonates and/or carbonates has also been found to be particularly advantageous for the incorporation of acid-sensitive active substances, such as for example H2-blockers such as ranitidine and famotidine. There was found to be a substantially lower tendency—especially also in a stress situation—on the part of the active substances to break down and to form decomposition products.

This system is also suitable for alkali-sensitive active substances in order to produce an effervescent tablet as it only requires small amounts of alkali hydrogen carbonates and/or carbonates in order to achieve rapid dissolution of the effervescent tablet.

EXAMPLES

The effervescent system according to the invention may have a pH of 3.9 to 4.3. Owing to the high dissolution rate, further amounts of sodium bicarbonate and also anhydrous sodium carbonate can also be added in order to avoid residue formation and to achieve a less acid pH for the effervescent tablet.

A final formulation for ranitidine hydrochloride is then as follows:

171 parts by weight of ranitidine hydrochloride,
2443 parts by weight of tartaric acid system according to the invention,
205 parts by weight of sodium bicarbonate,
128 parts by weight of sodium carbonate,
13 parts by weight of aspartame,
10 parts by weight of sodium chloride and
30 parts by weight of solid flavoring agent are pressed to give tablets having a tablet weight of 3 g.

It must be noted that this dry mixture can be pressed to give hardnesses up to 10 kp, whereas systems which were based on monosodium tartrate can scarcely be pressed with hardnesses above 3 kp without granulation.

The dissolution time is about 60 seconds and the pH 4.5.

EXAMPLES 2
Famotidine Effervescent Tablet 40 parts by weight of famotidine,
1056 parts by weight of tartaric acid effervescent system according to the invention,
89 parts by weight of sodium bicarbonate,
55 parts by weight of sodium carbonate,
30 parts by weight of sodium cyclamate,
3 parts by weight of saccharin sodium,
87 parts by weight of mannitol and
40 parts by weight of solid flavoring agent are pressed to give tablets having a tablet weight of 1200 mg. Dissolution time: about 40 seconds, pH: about 4.5

What is claimed is:

1. Process for preparing acidic components consisting essentially of monosodium tartrate for the forming of effervescent granules or tablets, characterized by the following steps:
   a) tartaric acid is mixed with sodium bicarbonate and sodium carbonate containing water of crystallization and slowly reacted at a temperature increasing to about 50° C., whereupon further sodium carbonate containing water of crystallization is admixed and allowed to react up to a temperature of about 60° C., and
   b) thereafter drying is carried out.

2. The process of claim 1 wherein the granules or tablets additionally comprise an acid sensitive or an alkali-sensitive pharmaceutically active substance.

3. The process for preparing acidic components according to claim 1, wherein the drying is carried out in vacuo.

* * * * *